(12) United States Patent
Busin

(10) Patent No.: US 6,789,544 B2
(45) Date of Patent: Sep. 14, 2004

(54) MODIFIED PENETRATING KERATOPLASTY METHOD

(76) Inventor: Massimo Busin, Via Sisa 33, Forlí FC (IT), 47100

( * ) Notice: Subject to any disclaimer, the term of this patent is extended or adjusted under 35 U.S.C. 154(b) by 0 days.

(21) Appl. No.: 10/247,708

(22) Filed: Sep. 20, 2002

(65) Prior Publication Data

US 2004/0059360 A1 Mar. 25, 2004

(51) Int. Cl.$^7$ .............................. A61B 19/00; A61F 2/14
(52) U.S. Cl. ........................................ 128/898; 623/5.11
(58) Field of Search ................................ 623/4.1, 5.11, 623/5.12–5.16; 128/97.1, 898

(56) References Cited

U.S. PATENT DOCUMENTS 5,647,865 A * 7/1997 Swinger ........................ 606/5
5,755,785 A * 5/1998 Rowsey et al. ............. 606/166

OTHER PUBLICATIONS

Assil, K. K. et al., "Visual Outcome After Penetrating Keratoplasty with Double Continuous or Combined Interrupted and Continous Suture Wound Closure", American Journal of Opthalmology, vol. 114, No. 1, Jul., 1992, pp. 63–71.*
Corneal Grafts, Edited by B.W. Rycroft, Butterworth & Co. (Publishers) Ltd., London, 1955, 99. 90–91.*
Assil, K. K. et al., "Visual Outcome After Penetrating Keratoplasty with Double Continuous or Combined Interrupted and Continous Suture Wound Closure", American Journal of Opthalmology, vol. 114, No. 1, Jul., 1992, pp. 63–71.*
Assil, K. K. et al., "Visual Outcome After Penetrating Keratoplasty with Double Continuous or Combined Interrupted and Continuous Suture Wound Closure", American Journal of Ophthalmology, vol. 114, No. 1, Jul., 1992, pp. 63–71.

Davis, Elizabeth A. et al., "Refractive and Keratometric Results after the Triple Procedure", Ophthalmology, vol. 105, No. 4, Apr. 1998, pp. 624–630.

Corneal Grafts, Edited by B. W. Rycroft, Butterworth & Co. (Publishers) Ltd., London, 1955, pp. 90–91.

* cited by examiner

Primary Examiner—Corrine McDermott
Assistant Examiner—Hieu Phan
(74) Attorney, Agent, or Firm—Nixon & Vanderhye P.C.

(57) ABSTRACT

A method of performing a penetrating keratoplasty in a living eye positions a full-thickness corneal graft obtained from a corneal donor in a full-thickness open bed in the recipient's cornea. The graft is held with a suture to prevent the graft from sliding out of position. Subsequently, the suture is removed. The corneal graft is circular, having a step-like edge-to-edge lateral profile with the diameter of the posterior surface being larger than the diameter of the anterior surface. The full-thickness open recipient bed is prepared to be essentially complementary to the donor corneal graft. The suture is lax to induce a post-operation astigmatism not higher than 4 dioptres (D). The suture is normally removed not later than three months from surgery.

13 Claims, 5 Drawing Sheets

MODIFIED PENETRATING KERATOPLASTY METHOD

FIELD OF THE INVENTION

The present invention relates to the technical field of corneal transplants (i.e. penetrating keratoplasty—PK). More precisely, the present invention relates to a new, modified method of performing PK carried out employing new means and new operation conditions.

BACKGROUND OF THE INVENTION

Although over the past decades PK surgery has undergone continuous refinement, said technique still needs several improvements.

Various instruments have been developed to improve the quality of trephination in both donor and recipient corneas, while countless suturing techniques have been employed to reduce tissue distortion and minimize postoperative refractive errors. Also donor grafts of different shape and profile have been envisaged in the past, which however did not find any practical application due to the lack of suitable means for their realization; see Corneal Grafts—Ed. B. W. Rycroft—Butterworth & Co. LTD Publisher—London—pp 90, 91, (1955).

Nevertheless, to date the basic concept of cutting a donor corneal disc with a "perfect" margin to fit a "perfect" hole in the recipient's cornea has remained unvaried.

According to the known conventional PK method a full-thickness "vertical" i.e. "edge to edge" wound is made in the recipient cornea. This results in a quasi-cylindrical open bed, which is filled in by a donor graft complementary in shape. Regardless of how donor and recipient cornea fit, this type of wound requires relatively tight sutures to hold the edges together until healing is sufficient to withstand the effect of the intraocular pressure. Said healing requires, usually, not less than one year.

As a consequence of said tight sutures, refraction is not stable and astigmatism, often of the irregular type, cannot be adequately corrected in a relatively high number of patients as long as sutures are present. In addition, when sutures are removed, substantial changes in refraction are frequently seen, possibly resulting in anisometropia and/or high-degree astigmatism. Finally, wound dehiscence occurs after suture removal in up to 4% of cases, even if removal is performed more than one year after surgery.

In spite the excellent prognosis of PK, visual rehabilitation of patients undergoing this type of procedure is slow and frequently hampered by high-degree astigmatism, often of the irregular type (K. K. Assi, S. R. Zarnegar, D. J. Schanzlin, "Visual Outcome after Penetrating Keratoplasty with Double Continuous or Combined Interrupted and Continuous Suture Wound Closure" Am. J. Ophthalmol.; 114 pages 63–71 (1992)). Several factors, including host-graft disparity, trephination technique, and suturing technique, are felt to affect the regularity of graft curvature. In addition, even if all other variables could be theoretically optimized, recovery of vision can be delayed by corneal distortion secondary to the presence of sutures, as some degree of tension-induced "tissue rolling" is necessary in order to obtain a watertight wound. Healing of these "vertical", edge-to-edge corneal wounds requires a minimum of 6 months and typically one year in adults. As a consequence, in a relatively high number of patients useful, stable vision is not achieved until many months after PK surgery, often not before suture removal (E. A. Davis et al. "Refractive and Keratometric Results after Triple Procedure. Experience with Early and Late Removal" Ophthalmology; 105, (1998) pages 624–630).

During recent years, different types of lamellar keratoplasty (LK) procedures have gained popularity among corneal surgeons in an attempt to transplant selected layers of the cornea, speeding wound healing while optimizing post-operative refraction. With these methods a "horizontal", surface-to-surface surgical wound results and the intraocular pressure tend to make the layers adhere to each other rather than gape. Tight suturing is not necessary and removal can be safely performed much earlier than after conventional PK surgery. However, the presence of a lamellar tissue interface may reduce the quality of vision after LK compared to that obtained with PK surgery.

The scope of the present invention is that of solving the problems inherent in the above-described techniques. More specifically, scope of the invention is to provide a novel PK method causing reduced post-operative anisometropia and/or astigmatisms and having quicker wound-healing as compared to the conventional PK method and, yet, not being affected by the low quality of vision typical of LK.

SUMMARY OF THE INVENTION

The present invention is based on the surprising finding that in a PK method, the specifically selected shape of the donor insert, the strength and position of the suture and the treatment conditions may result in a new method which unexpectedly combines the advantageous properties of PK with those of LK techniques, namely the final optical superiority offered by the former with the short healing time and reduced post-operation defects typical of the latter. The present invention modifies the conventional PK technique, first of all, in that a full thickness donor graft having a novel specific profile, shaped as a "reverse mushroom" (FIG. 1), is used to fill in the wound open in the recipient cornea and having complementary shape. Secondly, a lax suture is employed, which causes a reasonable, still acceptable, post-operation refractive astigmatism. Finally, the suture is removed as soon as a few months after surgery.

Hence, the object of the present invention is a method of performing a penetrating keratoplasty in living eye in which a full-thickness corneal graft obtained from a corneal donor is positioned in a full-thickness open bed in the recipient's cornea, the graft is held with suture to prevent sliding out of position, and the suture is finally removed, said corneal graft being circular, having step-like edge-to-edge lateral profile with the diameter of the posterior surface being larger than the diameter of the anterior surface, said full-thickness open recipient bed being prepared to be essentially complementary to the donor corneal graft and said suture being so lax to induce a post-operation astigmatism not higher than 4 dioptres (D). The suture is normally removed not later than three months from surgery.

In particular, the donor graft consists of a central full-thickness part, surrounded by a posterior circular peripheral wing of deep stroma and endothelium preferably about 1.0 mm in width. The diameter of the internal, posterior surface of the donor graft is preferably about 9.0 mm, and the diameter of the external, anterior surface of the donor graft is preferably about 7.0 mm.

The donor graft is held in position with suture in a way that each suture bite exits the donor graft at the base of the circular peripheral wing, and passes through the superficial recipient's lamellae at the end of the dissection so that the peripheral wing is left free to adhere to the posterior face of the dissected recipient's cornea under the effect of intraocular pressure.

In a further object of the invention the suture is stabilized or replaced in part or completely by biological glue or by internal anchoring means.

The method of the present invention brings about many advantages over the conventional PK methods as shown by the results reported in the experimental part of the application.

First of all, the shape of the donor graft, in combination with the exact position of the bites of suture, leaves the donor peripheral wings free to adhere to the posterior surface of the dissected recipient cornea under the effect of the intraocular pressure. This means that, upon post-suture injection of balanced salt solution into the anterior chamber, the surgical wound is perfectly watertight already at this point, and, more importantly, regardless of the strength of the suture. Under these circumstances, a lax suture technique is employed, which is simply intended to prevent the sliding out of position of the graft. As a consequence, the laxity of the suture reduces drastically the refractive post-operation astigmatism, which is normally maintained less than 4 Dioptres, even before removal of the suture.

Another advantage of the method of the invention is that the healing process is dramatically speeded up. This allows having a full-thickness graft completely free of suture as early as about four or three or even less months after surgery, thus significantly shortening the time necessary for visual rehabilitation.

A still further advantage is that, due to the particular shape of the donor graft a greater number of endothelial cells can be transplanted while maintaining the anterior graft surface at a safe distance from the corneo-scleral limbus. Finally, no expensive instrumentation is required for the method of the invention, except for artificial anterior chamber, if whole globes are not available.

Glossary

Donor graft: the portion of the donor's cornea to be transplanted, otherwise said donor button.

Recipient bed: the corneal incision in the recipient's living eye wherein the donor graft shall be placed.

Full-thickness: comprises all corneal layers.

Cardinal sutures: four sutures, each at one of the four cardinal points of the circular wound.

Circular running suture: a single suture along the complete circular wound.

DETAILED DESCRIPTION OF THE INVENTION

Figure 1:
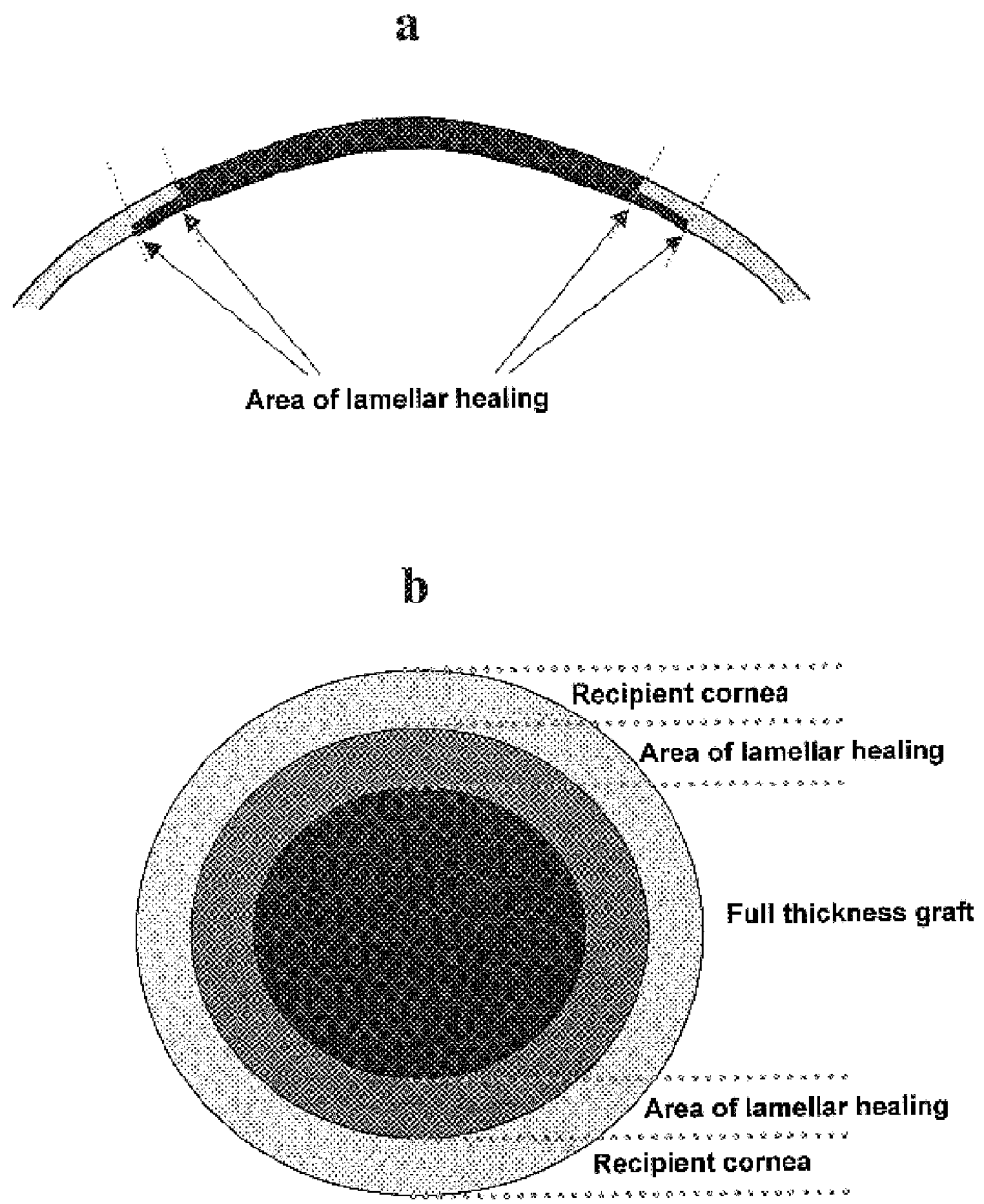
FIG. 1: Schematic representation of the cornea after a nut-and-bolt keratoplasty procedure. Both in the cross section (part a) and in the frontal view (part b) the annular area of lamellar healing is outlined between the recipient corneal bed outside and the full-thickness part of the graft inside.

The donor graft is the circular portion of the donor's cornea, which is transplanted into the recipient. The shape of the graft offers an essential contribution to the achievement of the advantageous effect obtained by the claimed method. Unlikely the graft inserts according to the conventional PK technology, which are quasi-cylindrical with vertical edge-to-edge lateral profile, the graft according to the invention shows a step-like lateral profile between the edges of the anterior (or external) face and the posterior (or internal) face. The graft consists essentially of a central full-thickness part surrounded at the internal side by a peripheral lamellar wing of deep stroma and endothelium, conferring the typical reverse mushroom shape (FIG. 1).

The size of the donor button varies according to the specific medical necessities. The diameter of the anterior surface (i.e. the external face of the full-thickness component of the graft) is from 5.5 to 7.5 mm, better from 6.0 to 7.3 mm, but it is preferably of about 7.0 mm.

The diameter of the posterior, internal surface of the donor graft is from 7.5 to 9.5 mm, better from 8.0 to 9.3 mm, but preferably it is of about 9.0 mm.

The peripheral wing of deep stroma and endothelium varies from 0.5 to 1.5 mm in width, better from 0.7 to 1.3 mm, but preferably it is about 1 mm in width. The thickness of the wing is about 0.3 mm less than the full-thickness of the donor cornea.

The diameters of both the full-thickness component and peripheral wing can be varied to achieve different purposes. The former can be cut smaller to reduce the possibility of immunological rejection trough contact with peripheral corneal neovascularization, while the latter could be made larger to increase the amount of endothelial cells transplanted. For instance patients undergoing the procedure reported in the examples received more donor endothelium (posterior surface of 9 mm in diameter) than patients operated with the conventional PK method (posterior surface of 7.5 to 8.5 mm in diameter). In converse, smaller grafts may be used in keratoconus patients (as little as about 5.5 mm for the external surface and about 7.5 mm for the internal surface), in order to leave the reservoir of endothelial cells in the recipient peripheral cornea as large as possible.

Also, the dimensional relationship between the two component of the graft (i.e. full-thickness part and wing) can be modified: a smaller full-thickness part with a larger peripheral wing could be fitted with even looser sutures or stabilized with the use of biological glue, which could replace completely or in part the suture.

The recipient bed open in the recipient cornea is essentially complementary to the donor graft shape. Its dimensions are either strictly complementary to the donor graft dimensions, or slightly larger than the full thickness part of the donor graft: even in this latter case, the surgical wound would still be watertight, due to the internal tamponade of the peripheral wing, and scar tissue would fill up the small space between donor and recipient thus preventing graft distortion. A gap of 0.1 to 0.2 mm between graft and bed is still acceptable.

Accordingly, the configuration of the open bed is that of a reverse mushroom having a circular opening on the anterior surface of the recipient's cornea with a diameter from 5.5 to 7.7 mm, preferably about 7.0 mm. The opening is surrounded by the superficial stromal lip, of 0.5 to about 1.5 mm, preferably about 1.0 mm in width, and about 0.3 mm in depth. The posterior part of the open bed will be also circular, with a diameter from 7.5 to 9.7 mm, preferably of about 9.0 mm.

Figure 2:
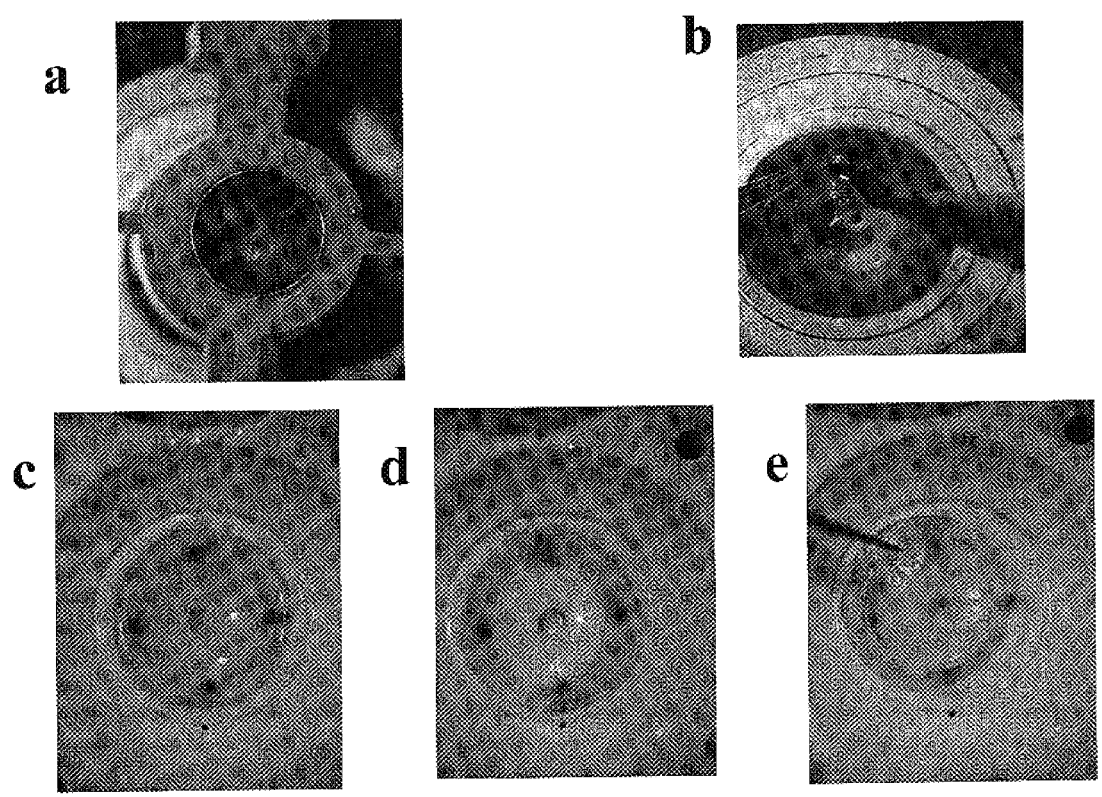
FIG. 2: Preparation of the donor graft. Partial trephination of the donor cornea mounted on the artificial chamber (part a); lamellar dissection from the base of the incision all the way to the limbus (part b); donor graft with the endothelial side up (part c); superficial annular stromal lamella removed from the donor graft (part d); donor graft consisting of a central, full-thickness part surrounded by a peripheral lamellar wing of deep stroma and endothelium (part e).

According to the present invention, the donor graft and the recipient bed can be prepared following any suitable manual or mechanical method and using any suitable means known and available to the person skilled in the art. The donor cornea is mounted on an artificial anterior chamber (Moria, Paris, France) after placing viscoelastic substance on the endothelium. The geometric center of the cornea is marked and a suction trephine (e.g. Barron trephine) is used to make a circular, about 0.3 mm deep incision (FIG. 2, part a). In accordance with the above-indicated sizes of the graft, the incision will be from 5.5 to 7.5 mm, preferably about 7.0 mm in diameter. A lamellar stromal dissection is carried out with a bevel-up knife from the base of the incision all the way to the limbus (FIG. 2, part b). Then the cornea is removed from the artificial anterior chamber and placed on the plate of a Barron suction punch with the endothelial side up, taking care to align the mark of the geometrical center with the central hole of the punch. Then, a donor graft of 7.5 to 9.5 mm, preferably about 9.0 mm in diameter, is punched out (FIG. 2, part c). As a result of the previous lamellar dissection, a superficial annular stromal lamella, 0.3 mm in thickness, can be removed in the area between the external and the internal diameter (FIG. 2, part d).

Figure 3:
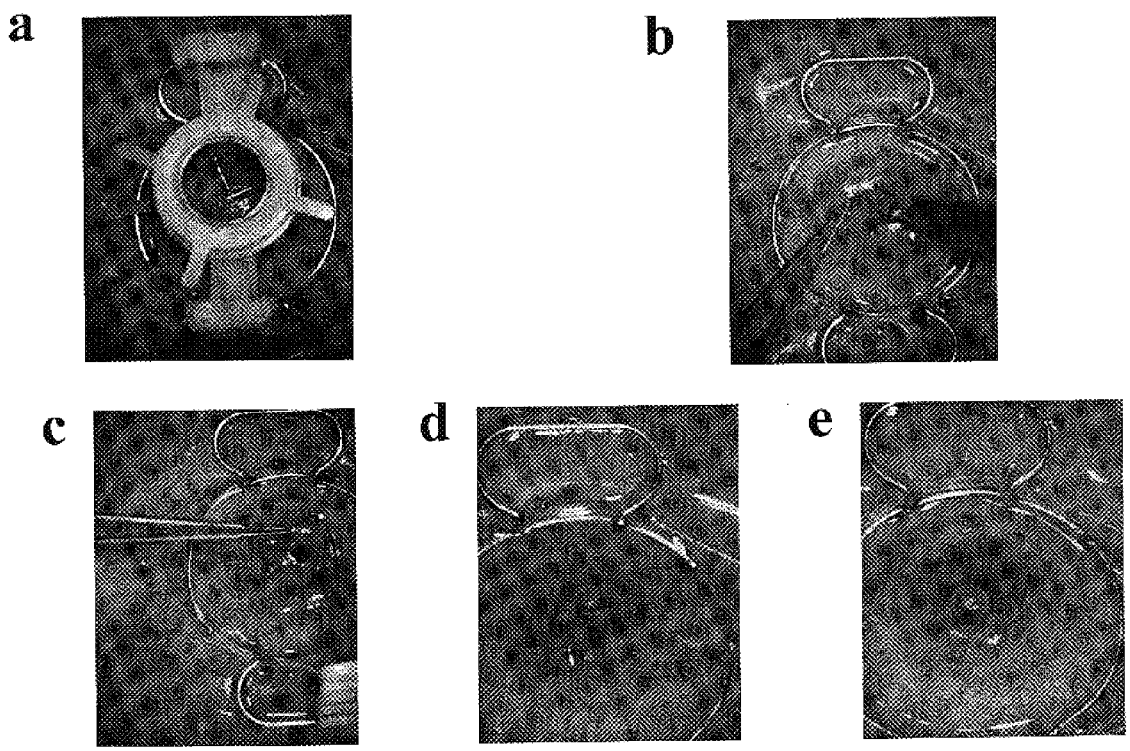
FIG. 3: Main surgical steps of the nut-and-bolt keratoplasty procedure. Partial trephination of the recipient bed (same as for the donor cornea) (part a); lamellar stromal dissection carried out from the base of the incision about 1 mm peripherally (part b); excision of the corneal button by means of corneal scissors placed at the peripheral end of the posterior lamellar stromal dissection (part c); injection of balanced salt solution into the anterior chamber shows that the surgical wound is perfectly water tight with just four cardinal sutures in place (part d); a single running 10-0 nylon suture is used to complete the procedure (part e).

The recipient bed is prepared so as to closely conform to the shape of the donor button. A McNeill-Goldman ring is used to fixate the globe. A Barron suction trephine is used to cut a circular incision, about 0.3 mm in depth (FIG. 3, part a). The trephination is from 5.5 to 7.7 mm, preferably 7.0 mm. A lamellar stromal dissection is carried out peripherally, with a bevel-up knife, from the base of the incision for 0.5 to 1.5 mm, preferably about 1 mm (FIG. 3, part b). The anterior chamber is then entered and corneal scissors are used to complete the excision of the corneal button at the peripheral end of the posterior lamellar stromal dissection (FIG. 3, c). The operation is carried out under suitable sedation condition and local anesthesia.

A further essential feature contributing to the achievement of the advantageous effects of the claimed method is the suture, specifically its location, the strength and removal.

Once prepared, the donor graft is firstly positioned within the open bed by sliding its peripheral wing under the superficial stromal lip of the recipient bed, and then it is held by way of suture.

Unlike the sutures used in the conventional PK, which are meant to render the wound watertight, the sutures used in the present method merely serve the purpose of preventing the donor graft from sliding out of position. In fact, the watertight effect is achieved thank to the intraocular pressure which tends to push the healing surfaces of graft peripheral wing and recipient stromal lip together. For this reason, the sutures need not to be as tight as they should be in order to seal the surgical wound.

However, in order to obtain this sealing effect, the type and position of the suture play an essential role.

Firstly, four cardinal sutures are placed to held the graft in the correct position. Then, a circular single running suture is performed along the whole perimeter of the wound. Finally, the four cardinal sutures are removed. Each bite of running suture needs to be exactly placed so that it exits the donor graft at the base of the peripheral wing and is then passed through the superficial recipient stromal lip or lamellae at the end of the dissection. This type of suture leaves the peripheral wing free to adhere to the posterior face of the dissected recipient cornea under the effect of the intraocular pressure.

Since the sealing effect is achieved thank to the nut-and-bold type of fitting between donor and recipient elements and to the exact location of the suture, the suture may be maintained much looser than in the conventional PK method. The strength or laxity of the suture is reflected by the higher or lower severity of the refractive astigmatism induced by the operation both before and after suture removal. Thus, according to the invention, the suture employed must be so lax, that it induces, both before and after its removal, a refractive error never exceeding 4 dioptres (D), but preferably remaining well below this limit.

Any type of suitable material may be used for suturing. The preferred type is yet a 10-0 nylon suture.

In a further embodiment of the invention, the suture may be stabilized or replaced in part or completely by biological glue or by internal anchoring means or devises contributing to keep the post-operation astigmatism even lower. Biological glue is fibrinogen glue or equivalent tissue compatible linking substance. Anchoring means or devises are pins, crowns, rings or ring fragments made of tissue compatible inert material, possibly absorbable, creating a fitting between donor and recipient parts. When pins, crowns, rings or ring fragments are used, these are located at the interface between donor and recipient parts, preferably between donor peripheral wing and recipient stromal lip, and are engaged, in suitable number, e.g. four or more, in respective sites open within the thickness of the corneal tissues.

Another important aspect of the claimed method is the removal of the suture. The suture must be kept only for a relatively short time after surgery. In fact, according to the claimed method, it is possible to have a graft completely free of sutures as early as a few months after surgery, that is, not later than four months, but preferably not later than three months or even earlier. This result is obtained because the intraocular pressure contribute to keep in close contact the healing surfaces of donor and recipient elements, facilitating, in this way, the healing mechanism, thus shortening the time necessary for recovery and visual rehabilitation. It is worthy to stress that in the conventional PK method, unlike in the claimed method, the intraocular pressure tends to extrude the donor insert and therefore, represents a bar, rather than a support, to wound healing.

Beginning the next morning post-operation, antibiotic, such as dexamethasone phosphate 0.1% and gentamicineye drops are administered every two hours and then tapered over 10-weeks.

The PK procedure according to the present invention finds application in the surgery treatment of e.g. endothelial decompensation such as aphakic bullous keratopathy; pseudophakic bullous keratopathy and Fuchs' endothelial corneal dystrophy. Moreover, the method can be performed in combination with other surgical procedures such as, anterior vitrectomy, anterior vitrectomy combined with the exchange of the intraocular lens implant (IOL), anterior vitrectomy combined with IOL implantation, pupilloplasty.

The invention is further illustrated in all details by the description of the following experimental work carried out on 8 patients suffering from endothelial decompensation.

Patients: Eight patients suffering from endothelial decompensation, that is aphakic bullous keratopathy n=1; pseudophakic bullous keratopathy n=6; and Fuchs' endothelial corneal dystrophy n=1 were treated according to the modified PK procedure of the invention.

A detailed informed consent was signed by all eight patients undergoing surgery. Sedation by intravenous droperidol 3 ml immediately prior to anesthetic injection was administered in all cases. Local anesthesia was achieved with peribulbar injection of a mixture of 2% lidocaine and 0.5% bupivicaine.

Preoperatively, the medical history of each patient was recorded and a complete eye examination was performed, including visual acuity, slit-lamp examination, retinoscopy, as well as B-scan ultrasonography when necessary (n=2). Details regarding preoperative data are given in Table 1. Postoperatively, patients were seen twice a week until re-epithelialization was completed, which occurred within two weeks from surgery in all cases. Uncorrected visual acuity was measured every week postoperatively. One month after surgery patients were refracted, and both uncorrected and best-spectacle corrected visual acuity were determined. In addition, keratometry and corneal topography analysis were obtained. Monthly examinations were performed thereafter. Sutures were removed 3 months after surgery in all cases. Each patient underwent a repeat complete eye examination one month after suture removal.

Surgical Technique: The donor cornea was mounted on an artificial anterior chamber (Moria, Paris, France) after placing viscoelastic substance on the endothelium. The geometric center of the cornea was marked and a Barron 7.0 mm suction trephine was used to make a circular, 0.3 mm deep incision (FIG. 2, part a). A lamellar stromal dissection was carried out with a bevel-up knife from the base of the incision all the way to the limbus (FIG. 2, part b). Then the cornea was removed from the artificial anterior chamber and placed on the plate of a Barron suction punch with the endothelial side up, taking care to align the mark of the geometrical center with the central hole of the punch. A 9.0 mm donor graft was punched out (FIG. 2, part c). As a result of the previous lamellar dissection, a superficial annular stromal lamella, 0.3 mm in thickness, could be removed in the area between 7.0 and 9.0 mm of diameter (FIG. 2, part d). The donor graft obtained this way consisted of a central, full-thickness part, 7.0 mm in diameter, surrounded by a peripheral lamellar wing of deep stroma and endothelium, 1.0 mm in width (FIG. 2, part e). A McNeill-Goldman ring was used to fixate the globe. The recipient bed was prepared so as to closely conform to the shape of the donor graft. A 7.0 mm Barron suction trephine was used to cut a circular incision, 0.3 mm in depth (FIG. 3, part a). A lamellar stromal dissection was carried out, with a bevel-up knife, from the base of the incision about 1 mm peripherally (FIG. 3, part b). The anterior chamber was then entered and corneal scissors were used to complete the excision of the corneal button at the peripheral end of the posterior lamellar stromal dissection (FIG. 3, part c). The donor graft was positioned by sliding the peripheral wing under the 1.0 mm wide superficial stromal lip of the recipient bed. Four 10-0 nylon cardinal sutures were first placed. Each suture exited the donor at the base of the wing and was then passed through the superficial recipient lamellae at the end of the dissection. Contrary to what is typically observed with conventional PK surgery, injection of balanced salt solution into the anterior chamber showed that the surgical wound was perfectly water tight already at this point (FIG. 3, part d). The procedure was completed with a single 10-0 nylon-running suture, each bite of which was passed in a fashion similar to what described above for the cardinal sutures. Finally, the cardinal sutures were removed (FIG. 3, part e). After surgery the patients were pressure-patched overnight. Beginning the next morning, dexamethasone phosphate 0.1% and gentamicin antibiotic eye drops were administered every two hours and then tapered over 10-weeks.

Results: Surgery was uneventful in all patients. All corneas gradually cleared over time and reepithelialization was completed within two weeks from surgery. Preoperative data, as well as those recorded one month after surgery and one month after suture removal are summarized in tables 1 to 3.

TABLE 1

| Patient Nr. | 1 | 2 | 3 | 4 | 5 | 6 | 7 | 8 |
|---|---|---|---|---|---|---|---|---|
| Age | 68 | 81 | 94 | 63 | 77 | 78 | 72 | 84 |
| Sex | Male | Male | Female | Female | Male | Female | Female | Female |
| Preoperative Diagnosis | PBK | PBK | PBK | Fuchs' dystrophy | PBK | PBK | PBK | ABK |
| Preoperative VA* | HM | HM | CF | HM | HM | CF | CF | HM |

Table 1: Preoperative data collected from patients undergoing modified PK surgery.

PBK=pseudophakic bullous keratopathy;

ABK=aphakic bullous keratopathy;

VA=visual acuity (*not improvable due to corneal edema).

TABLE 2

| Patient Nr. | 1 | 2 | 3 | 4 | 5 | 6 | 7 | 8 |
|---|---|---|---|---|---|---|---|---|
| UCVA | 20/200 | 20/100 | 20/60 | HM | 20/100 | 20/60 | 20/50 | 20/200 |
| BCVA | 20/60 | 20/60 | 20/40 | 20/200 | 20/60 | 20/50 | 20/40 | 20/100 |
| SE | −1.75 | −1.25 | −0.50 | −8.50 | −1.50 | +0.75 | −0.50 | −1.00 |
| RA | 2.25 | 1.50 | 1.00 | 4.00 | 3.00 | 2.00 | 1.00 | 2.75 |
| K-Reading | 44.50 | 43.00 | 42.50 | 40.50 | 41.25 | 41.00 | 42.75 | 42.50 |

Table 2: Data collected from patients undergoing 10 modified PK surgery, 1 month postoperatively.

UCVA=uncorrected visual acuity; BCVA=best-corrected visual acuity; SE=spherical equivalent (in diopters); RA=refractive astigmatism (in diopters); K-reading= mean keratometry-reading (in diopters);

TABLE 3

| Patient Nr. | 1 | 2 | 3 | 4 | 5 | 6 | 7 | 8 |
|---|---|---|---|---|---|---|---|---|
| UCVA | 20/100 | 20/200 | 20/50 | HM | 20/100 | 20/60 | 20/50 | 20/100 |
| BCVA | 20/60 | 20/60 | 20/40 | 20/200 | 20/40 | 20/30 | 20/25 | 20/100 |
| SE | −2.25 | −1.50 | −0.50 | −7.50 | −1.75 | +1.00 | −1.00 | −1.00 |
| RA | 2.50 | 1.75 | 0.75 | 4.00 | 3.00 | 1.50 | 1.00 | 2.25 |
| K-Reading | 44.75 | 43.00 | 43.00 | 40.50 | 42.00 | 41.00 | 43.00 | 42.50 |

Table 3: Data collected from patients undergoing modified PK surgery 1 month after suture removal. UCVA=uncorrected visual acuity; BCVA=best-corrected visual acuity; SE=spherical equivalent (in diopters); RA=refractive astigmatism (in diopters); K-reading=mean keratometry-reading (in diopters).

Figure 4:
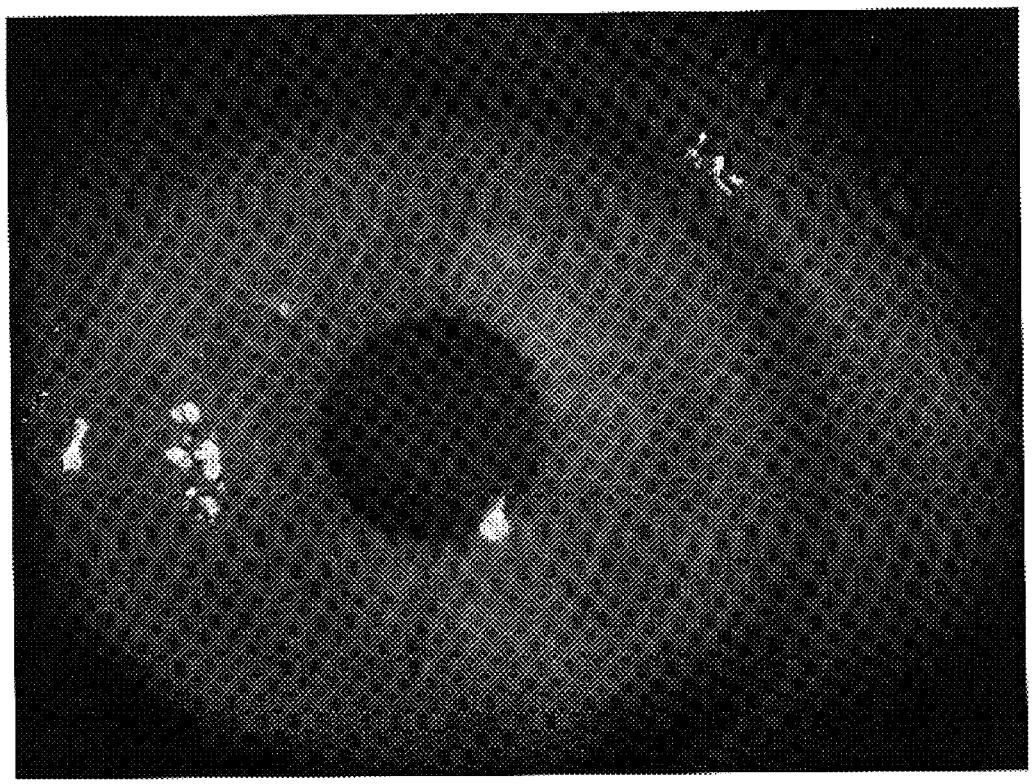
FIG. 4: Clinical picture of patient Nr. 4 in this series, one day after suture removal. The graft is crystal clear in its full-thickness part, surrounded by the hazier annular area of lamellar healing.
Figure 5:
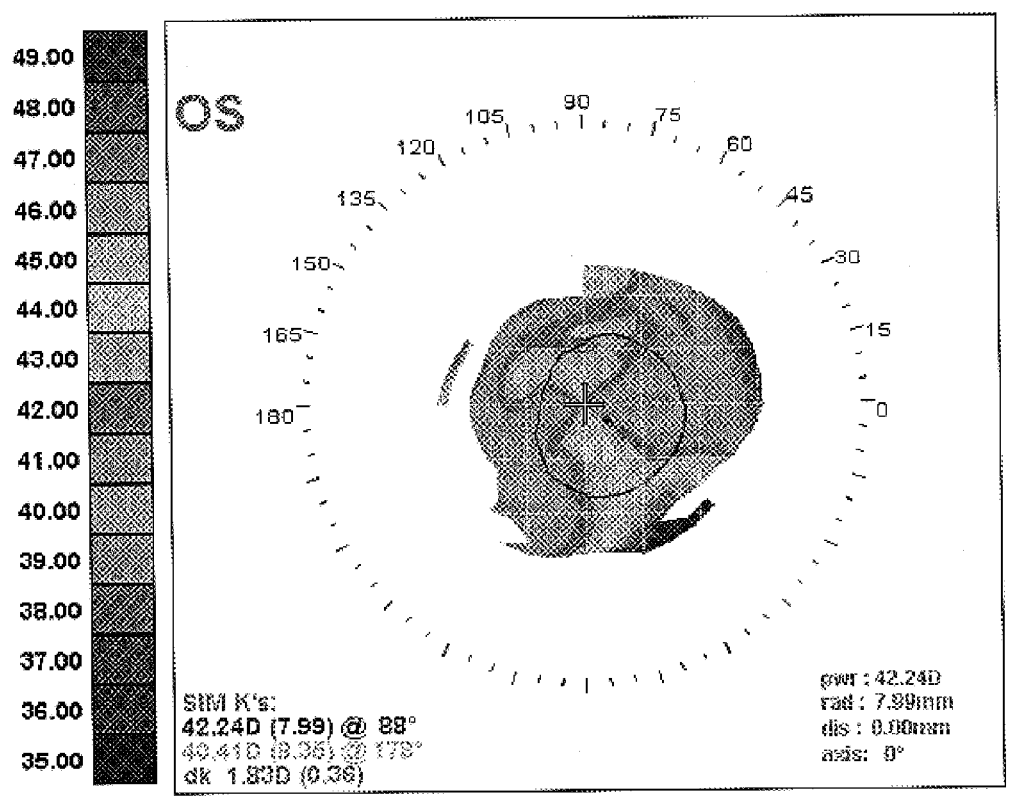
FIG. 5: Computerized analysis of corneal topography of a patient performed 1 month after suture removal shows the presence of a low-degree, regular astigmatism.

The 10-0 nylon running suture was removed 3 months after surgery in all patients (FIG. 4). As early as one month after surgery (table 2), useful uncorrected vision of at least 20/200 was recorded in each patient except one (Nr. 4 in the tables) suffering from high-degree myopia. Spectacle best-corrected visual acuity ranged between 20/100 and 20/40. One month after suture removal (table 3), both uncorrected and spectacle best-corrected visual acuity further improved and 6 of 8 patients could see 20/60 or better with spectacle correction. Reasons for best-corrected vision below 20/60 were macular myopic degeneration (patient Nr. 4) and cystoid macular edema (patient Nr. 8). At one month after surgery (table 2), the refractive spherical equivalent ranged from +0.75 dioptres (D) to −8.50 D. Mean keratometric readings ranged from 40.50 D to 44.50 D. The refractive astigmatic error was less than 4.00 D in all cases. Computerized analysis of corneal topography showed the presence of a regular morphology of the astigmatism in all patients at all examination times (FIG. 5). Quite surprisingly, suture removal did not substantially affect refraction in any patient of this series (table 3). Again, refractive astigmatism was less than 4 D in all cases. It must be noticed, that the patient Nr. 4's preoperative spectacle cylinder was 4 D.

In conclusion our data show that a lamellar wound construction based on the nut-and-bold concept optimizes post-keratoplasty refractive error while substantially speeding-up visual recovery. Although post-operative follow-up of these patients was relatively short, significant data were obtained one month after suture removal, a time after which no substantial changes in refraction are usually seen with conventional PK surgery.

What is claimed is:

1. A method of performing a penetrating keratoplasty in a living eye, the method comprising:
   providing a full-thickness circular corneal graft obtained from a corneal donor and having a step-like edge-to-edge lateral profile with a diameter of its posterior surface being larger than a diameter of its anterior surface;
   preparing a full-thickness open recipient bed in a recipient's cornea so as to be essentially complementary to the donor corneal graft;
   positioning the full-thickness corneal graft in the full-thickness open bed;
   securing the graft with a suture solely to prevent the graft from sliding out of position, the suture being lax enough to induce a post-operation astigmatic error not higher than 4 dioptres; and
   removing the suture not later than three months from surgery.

2. Method according to claim 1, wherein the donor graft comprises a central full-thickness part, surrounded by a posterior circular peripheral wing of deep stroma and endothelium 0.5 to 1.5 mm in width.

3. Method according to claim 2, wherein the diameter of the posterior surface of the donor graft is from 7.5 to 9.5 mm and the diameter of the anterior surface of the donor graft is from 5.5 to 7.5 mm.

4. Method according to claim 1, wherein the recipient bed dimensions are either strictly complementary to the donor graft dimensions, or 0.1 to 0.2 mm larger than the donor graft size.

5. Method according to claim 1, wherein four cardinal sutures are placed, then a circular single running suture is performed and, finally the four cardinal sutures are removed.

6. Method according to claim 1, wherein each suture bite exits the donor graft at the base of the circular peripheral wing, and passes through the superficial recipient's stromal lip at the end of the dissection so that the peripheral wing is left free to adhere to the posterior face of the dissected recipient's cornea under the effect of intraocular pressure.

7. Method according to claim 1, wherein a donor graft is prepared in that the donor's cornea is mounted on an artificial anterior chamber, the geometric centre of the cornea is marked, a suction trephine of about 7.0 mm is used to make a circular about 0.3 mm deep incision, a lamellar stromal dissection is carried out from the base of the incision all the way to the limbus, then, the cornea is removed from the artificial anterior chamber and placed on the plate of a suction punch with the endothelial side up with the mark of the geometrical centre aligned with the central hole of the punch, an about 9.0 mm donor graft is punched out and the superficial annular stromal lamella about 0.3 mm in thickness is than removed.

8. Method according to claim 1, wherein the recipient bed is prepared in that an about 7.0 mm suction trephine is used to cut a circular incision about 0.3 mm in depth on the recipient's cornea external surface, a lamellar stromal dissection of about 1.0 mm is carried out from the base of the incision, then, the anterior chamber is entered and the excision of the recipient's corneal button is completed using corneal scissors so that the internal surface of the recipient's cornea presents a circular incision of about 9.0 mm.

9. Method according to claim 1, wherein the suture is either stabilized or replaced in part or completely by a biological glue or by internal anchoring means.

10. Method according to claim 9, wherein the biological glue is a fibrinogen glue or equivalent substance.

11. Method according to claim 9, wherein anchoring means are pins of tissue compatible material engaged in respective sites located within the thickness of the donor peripheral wing and the recipient stromal lip.

12. Method according to claim 9, wherein anchoring means are crowns or rings or ring segments of tissue compatible material creating a stabilizing fitting between donor and recipient parts.

13. A penetrating keratoplasty performed in a living eye according to the method of claim 1.

* * * * *

UNITED STATES PATENT AND TRADEMARK OFFICE
CERTIFICATE OF CORRECTION

PATENT NO.     : 6,789,544 B2
DATED          : September 14, 2004
INVENTOR(S)    : Busin et al.

It is certified that error appears in the above-identified patent and that said Letters Patent is hereby corrected as shown below:

Title page,
Delete Item "[76] Inventor: Massimo Busin, Via Sisa 33, Forli FC (IT), 47100A" and insert therefor
-- [76] Inventors: Massimo Busin, Via Sisa 33, Forli FC (IT), 47100A and Robert C. Arffa, 709 Ridgefield Avenue, Pittsburgh, Pennsylvania (US) 15216 --.

Signed and Sealed this

Sixteenth Day of November, 2004

JON W. DUDAS
*Director of the United States Patent and Trademark Office*